(12) United States Patent
Schmitt et al.

(10) Patent No.: US 7,790,908 B2
(45) Date of Patent: Sep. 7, 2010

(54) PROCESS FOR PREPARING GLYCERYL CARBONATE

(75) Inventors: Bardo Schmitt, Mainz (DE); Joachim Knebel, Alsbach-Haehnlein (DE); Maik Caspari, Alsbach-Haehnlein (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 12/088,093

(22) PCT Filed: Oct. 11, 2006

(86) PCT No.: PCT/EP2006/067279

§ 371 (c)(1),
(2), (4) Date: Mar. 26, 2008

(87) PCT Pub. No.: WO2007/071470

PCT Pub. Date: Jun. 28, 2007

(65) Prior Publication Data

US 2008/0255372 A1 Oct. 16, 2008

(30) Foreign Application Priority Data

Dec. 16, 2005 (DE) .................. 10 2005 060 732

(51) Int. Cl.
*C07D 317/34* (2006.01)

(52) U.S. Cl. .................. 549/228; 549/229; 549/230

(58) Field of Classification Search .................. 549/228, 549/229, 230
See application file for complete search history.

(56) References Cited

U.S. PATENT DOCUMENTS 2,915,529 A 12/1959 Bell, Jr. et al.
5,359,094 A * 10/1994 Teles et al. .................. 549/228

FOREIGN PATENT DOCUMENTS

| EP | 0 478 073 | 4/1992 |
| EP | 0 739 888 | 10/1996 |
| JP | 06 329663 | 11/1994 |
| WO | 03 042141 | 5/2003 |

OTHER PUBLICATIONS

U.S. Appl. No. 11/995,406, filed Jan. 11, 2008, Schmitt, et al.
U.S. Appl. No. 12/093,744, filed May 15, 2008, Schmitt, et al.
U.S. Appl. No. 12/092,507, filed May 2, 2008, Klesse, et al.
U.S. Appl. No. 61/014,927, filed Dec. 19, 2007, Karnbrock.
U.S. Appl. No. 12/159,871, filed Jul. 2, 2008, Wiesler, et al.

* cited by examiner

*Primary Examiner*—Janet L Andres
*Assistant Examiner*—David E Gallis
(74) *Attorney, Agent, or Firm*—Oblon, Spivak, McClelland, Maier & Neustadt, L.L.P.

(57) ABSTRACT

The present invention relates to a process for preparing highly pure glyceryl carbonate by transesterifying dialkyl carbonates or cyclic carbonates in the presence of a basic catalyst.

17 Claims, No Drawings

PROCESS FOR PREPARING GLYCERYL CARBONATE

The invention relates to a process for preparing glyceryl carbonate with low glycerol content.

Glyceryl carbonate is used as an intermediate to prepare pharmaceuticals and pesticides and to prepare (meth)acrylates as a precursor for coating resins. A high purity is therefore advantageous.

U.S. Pat. No. 2,915,529 describes a complicated process for preparing glyceryl carbonate from ethylene carbonate and glycerol with NaOH. In a 2-stage process, the pH is adjusted, then the low boilers are distilled off and, after a further addition of catalyst, reaction is continued and distillation is repeated. The statement of the purity of 97.5% also does not include any data on the type of by-products. The presence of glycerol in particular presents problems in the further processing, since the functionalization of the hydroxyl group, for example by the reaction with polyisocyanates, causes undesired side reactions, preferably crosslinking reactions or oligomerizations, to take place.

EP 739888 describes a process for preparing glyceryl carbonate from ethylene carbonate and glycerol with Amberlyst (ion exchanger) or zeolites, in which 2-4% glycerol is present in the crude product.

JP 2001172277 claims the preparation of glyceryl carbonate by transesterifying dimethyl carbonate with glycerol under basic catalysis. The glyceryl carbonate has a glycerol content of 1.6% at a purity of 95%.

EP 1423377 describes purification of glyceryl carbonate by means of anhydrous base. The work up step lowers the glycerol content to 3.5-4.1% by weight.

As well as the additional working step, the work up is also associated with a yield loss.

It was an object of the invention to prepare glyceryl carbonate in high purity and with high yields.

The object is achieved by a process for preparing glyceryl carbonate, characterized in that glycerol is transesterified with dialkyl carbonates or cyclic carbonates in the presence of a basic catalyst composed of a mixture of at least two components from the group of the metal hydroxides and/or chlorides and/or oxides.

It has been found that, surprisingly, the resulting crude product comprises only small amounts of glycerol.

It has been found that the high purity of the crude product, especially the low content of glycerol, allows a purification step to be dispensed with. This allows a process step to be saved and the yield additionally to be increased.

The starting materials used are dialkyl carbonates, preferably dimethyl carbonate or diethyl carbonate.

It is also possible to use cyclic carbonates, preferably ethylene carbonate.

The basic catalyst or the catalyst mixture is used in amounts of 0.01 to 10% by weight.

The basic catalysts used from the group of the alkali metal or alkaline earth metal hydroxides, chlorides and/or oxides are preferably mixtures of 2 or 3 components from the group of lithium hydroxides or potassium hydroxides or calcium hydroxides and/or lithium chlorides or potassium chlorides or calcium chlorides and/or calcium oxides.

Preference is given to using mixing ratios of hydroxides to oxides of 1:99% to 99:1%, more preferably 15:85% to 30:70%, preferably of 28:72% for LiOH:CaO.

Preferred mixing ratios for chlorides with hydroxides are 1:99% to 99:1%, more preferably 15:85% to 30:70%, preferably 20:80% for LiCl:Ca(OH)$_2$.

Preferred mixing ratios for chlorides with oxides are 1:99% to 99:1%, more preferably 15:85% to 30:70%, preferably 20:80% for LiCl:CaO.

The transesterification is effected at temperatures of 60-150° C., preferably at 70-85° C.

The transesterification is effected under standard pressure. However, attempts to transesterify under reduced pressure were also successful. It is equally possible to work under elevated pressure.

Fields of use for glyceryl carbonate prepared by the process according to the invention are, for example, as a precursor for coatings and adhesives.

The examples given below are given for better illustration of the present invention but are not capable of restricting the invention to the features disclosed herein.

EXAMPLES

Example 1 (B1)

46.1 g of anhydrous glycerol from Merck=0.5 mol
180.2 g of dimethyl carbonate from Merck=2.0 mol
1.1 g of mixed catalyst=0.5% based on batch
(28% LiOH/72% CaO)

The batch is introduced into the reaction apparatus and heated under reflux for 9 hours. After cooling, the catalyst is removed by filtration. The low boilers are then distilled off under reduced pressure on a rotary evaporator, then the mixture is filtered once again and the crude product is obtained.

Example 2 (B2)

276.6 g of anhydrous glycerol from Merck=3.0 mol
1081.2 g of dimethyl carbonate from Merck=6.0 mol
6.6 g of mixed catalyst=0.5% based on batch
(28% LiOH/72% CaO)

The batch is introduced into the reaction apparatus and heated under reflux for 8 hours. After cooling, the catalyst is removed by filtration. The low boilers are then distilled off under reduced pressure on a rotary evaporator, then the mixture is filtered once again and the crude product is obtained.

Example 3 (B3)

46.1 g of anhydrous glycerol from Merck=0.5 mol
180.2 g of dimethyl carbonate from Merck=2.0 mol
1.1 g of mixed catalyst=0.5% based on batch
(20% LiCl/80% Ca(OH)$_2$)

The batch is introduced into the reaction apparatus and heated under reflux for 8 hours. After cooling, the catalyst is removed by filtration. The low boilers are then distilled off under reduced pressure on a rotary evaporator, then the mixture is filtered once again and the crude product is obtained.

Example 4 (B4)

46.1 g of anhydrous glycerol from Merck=0.5 mol
180.2 g of dimethyl carbonate from Merck=2.0 mol
1.1 g of mixed catalyst=0.5% based on batch
(20% LiCl/80% CaO)

The batch is introduced into the reaction apparatus and heated under reflux for 8 hours. After cooling, the catalyst is removed by filtration. The low boilers are then distilled off under reduced pressure on a rotary evaporator, then the mixture is filtered once again and the crude product is obtained.

Experiments for the Preparation of Glyceryl Carbonate

| Experiment No. | Catalyst % based on batch | Glycerol mol | DMC* mol | Reaction Temp. C. | Time h | Glycerol area % | DMC area % | GMDC* | Product area % | Mass Appearance |
|---|---|---|---|---|---|---|---|---|---|---|
| B1 | Li-lime: LiOH/CaO (28%/72%) 0.5% | 0.5 | 2 | 80-76 | 9 | 0.20 | — | 2.6 | 96.1 | 60 g colourless, clear |
| B2 | Li-lime: LiOH/CaO (28%/72%) 0.5% | 3.0 | 12.0 | 77-73 | 8 | 0.05 | — | 2.0 | 95.8 | 354 g colourless, clear |
| B3 | Modified Li-lime LiCl/Ca(OH)$_2$ (20%/80%) 0.005 | 0.5 | 2 | 80-74 | 8 | 0.80 | — | 2.2 | 95.2 | 59 g colourless, clear |
| B4 | LiCl/CaO (20%/80%) 0.005 | 0.5 | 2 | 80-74 | 8 | 0.14 | — | 0.5 | 97 | 56 g colourless, clear |

DMC* = dimethyl carbonate
*further peaks not taken into account
GMDC—glyceryl methyldicarbonate
n.d. = not determined Examples B1, B2, B3 and B4 show high product yields and very low glycerol contents in the product. Example 4 additionally shows a low concentration of glyceryl methyldicarbonate.

The invention claimed is:

1. A process for preparing glyceryl carbonate, comprising:
   transesterifying at least one dialkyl carbonate or cyclic carbonate in the presence of a basic catalyst comprising a mixture of at least two of (A), (B) and (C),
   wherein (A) is at least one metal hydroxide, (B) is at least one metal chloride, and (C) is at least one metal oxide, thus producing glyceryl carbonate;
   wherein (A) is a hydroxide of, (B) is a chloride of, and (C) is an oxide of, at least one alkali metal and/or alkaline earth metal.

2. The process of claim 1, wherein (A), (B) and (C) are, respectively, at least one hydroxide, at least one chloride, and at least one oxide, of at least one alkali metal.

3. A process for preparing glyceryl carbonate, comprising:
   transesterifying at least one dialkyl carbonate or cyclic carbonate in the presence of a basic catalyst comprising LiCl/CaO.

4. The process of claim 1, wherein said basic catalyst is used in an amount ranging from 0.01 to 10% by weight.

5. The process of claim 1, wherein said basic catalyst comprises a mixture of hydroxides and oxides, chlorides and hydroxides, or chlorides and oxides, in a ratio of 1:99% to 99:1%.

6. The process of claim 1, wherein the transesterification is effected at 60-150° C.

7. The process of claim 1, wherein the transesterification is effected under standard pressure or under reduced pressure.

8. The method of claim 1, comprising transesterifying at least one dialkyl carbonate.

9. The method of claim 1, comprising transesterifying at least one cyclic carbonate.

10. The method of claim 1, comprising transesterifying dimethyl carbonate or diethyl carbonate, or both.

11. The method of claim 1, comprising transesterifying ethylene carbonate.

12. The method of claim 1, wherein (A), (B) and (C) are, respectively, at least one hydroxide, at least one chloride, and at least one oxide, of at least one alkaline earth metal.

13. The method of claim 1, wherein the basic catalyst is a mixture of at least two of (A), (B) and (C):
   (A) a hydroxide selected from the group consisting of lithium hydroxide, potassium hydroxide or calcium hydroxide;
   (B) a chloride selected from the group consisting of lithium chloride, potassium chloride or calcium chloride; and
   (C) calcium oxides.

14. The method of claim 13, wherein said basic catalyst is a mixture of (A), (B) and (C).

15. The method of claim 1, wherein said basic catalyst is LiOH:CaO.

16. The method of claim 1, wherein said basic catalyst is LiCl:Ca(OH)$_2$.

17. The method of claim 1, wherein said basic catalyst is LiCl:CaO.

* * * * *